United States Patent [19]
Lanham et al.

[11] 4,072,575
[45] Feb. 7, 1978

[54] BROTH AND METHOD FOR DETECTING E. COLI IN MIXED WATER SAMPLES

[75] Inventors: James W. Lanham, St. Louis; Ralph A. Wilkinson, Florissant; Victoria A. Dagy, St. Louis, all of Mo.

[73] Assignee: McDonnell Douglas Corporation, St. Louis, Mo.

[21] Appl. No.: 682,253

[22] Filed: May 3, 1976

[51] Int. Cl.$^2$ .............................................. C12K 1/04
[52] U.S. Cl. .......................... 195/103.5 M; 195/100
[58] Field of Search ................. 195/99, 100, 101, 102, 195/103, 103.5 R, 103.5 M

[56] References Cited
PUBLICATIONS

Robert Bailey and Elwyn Scott; Diagnostic Microbiology, Second Ed., the C. V. Mosby Company; 1966; pp. 26, 295 and 296.

*Primary Examiner*—Lionel M. Shapiro
*Assistant Examiner*—Robert J. Warden
*Attorney, Agent, or Firm*—Gravely, Lieder & Woodruff

[57] ABSTRACT

A broth medium for the detection of *Escherichia coli* in water samples, i.e., sewage specimens, and process for inoculation and incubation of said broth to conduct satisfactory detection tests. The medium employs paracoumaric acid and acetazolamide to inhibit growth of unwanted microorganisms and thus greatly reduces false positive test results.

8 Claims, No Drawings

BROTH AND METHOD FOR DETECTING E. COLI IN MIXED WATER SAMPLES

BACKGROUND OF THE INVENTION

*Escherichia coli (E. coli)* is a gram negative bacterium which occurs naturally in the intestinal tract of warm-blooded animals. The presence of this bacterium in water is a reliable indicator of fecal contamination. If *E. coli* bacterium is present in a given sample of water, it is also possible that Salmonella, Shigella, Vibrio, enteric viruses, and intestinal parasites are also present in the sample.

No reliable single step process is known to detect the presence of *E. coli* in a sample of water containing mixed bacteria. Currently a two-step process is used to detect this microorganism. In this process a broth culture is inoculated with the water sample and then incubated at 35° C and examined for gas production after 24 and 48 hours. The gas is detected in Durham tubes, which are small test tubes inverted in the culture broth and filled with the culture medium. As the gas is being produced, it is collected in the Durham tubes. The gas becomes visible as a bubble in the Durham tube. It is presumed that the tubes which contain gas bubbles have detected *E. coli*. Growth from these tubes are then transferred to fresh broth in which are immersed other Durham tubes. The specimens are incubated at 44.5° C for an additional 24 hours and those tubes which produce gas at 44.5° C are termed "Positive". Under present practice, it is presumed the gas producing tubes represent confirmation that *E. coli* was present in the water sample tested. Over the past 20 years it has become evident to those working in the art that many of the Durham tubes which indicated "Positive" results did not actually contain *E. coli*. The tubes were rendered "Positive" by microorganisms such as Klebsiella, Enterobacter and Citrobacter. Because these microorganisms are also found in the intestinal tract, the term "Fecal Coliform" was coined to describe microorganisms which produce gas at 44.5° C in the aforementioned two-step process. However, it is now known that several of the Klebsiella and Enterobacter organisms which give "Positive" results in the current tests at 44.5° C are not of fecal origin, but are normal inhabitants of soil, water, and plants.

We have discovered a process which does not depend on gas production to detect *E. coli* in water samples. Our process involves neither transfer of positive Durham tube cultures to a second culture broth nor a second incubation step. We have discovered a culture medium and a single step method wherein the medium is inoculated with the water sample, incubated at about 35° to about 38° C for about 4 to about 6 hours, and then incubated at about 44° to about 46° C for about 10-12 hours. Positive results are indicated by means of a change in color of a pH indicator solution incorporated into the medium. The entire test can be completed within 16 to 20 hours, whereas current methods of detection require from 36 to 48 hours. Our test requires only one tube per culture whereas current methods require two tubes per culture. Our test also eliminates the use of Durham tubes, which are both costly and time consuming. Furthermore our test gives a far better percentage indication of *E. coli* than do current methods because most Klebsiella and Enterobacter species which normally grow and produce acid (gas) at 44.5° C are inhibited by para-coumaric acid and acetazolamide, and thus do not grow at this elevated temperature.

SUMMARY OF THE INVENTION

This invention involves a broth medium for the detection of *E. coli* in water samples and a process for inoculation and incubation of said broth to conduct satisfactory detection tests.

The medium contains a mixture of coumaric acid and acetazolamide to inhibit growth of Klebsiella, nutrients including lactose which is fermented by *E. coli* to produce acids, a surfactant to inhibit gram positive organisms, and a biological indicator responsive to changes in pH produced by action of *E. coli* on lactose.

DETAILED DESCRIPTION

The detection broth of the present invention contains from 1.19 to 4.28% nutrients, about 0.005 to about 0.025% of an indicator which indicates the positive growth of *E. coli* organism, in combination, about 0.03 to about 0.08% paracoumaric acid (para-hydroxy-phenyl acrylic acid) and about 0.05 to about 0.20% acetazolamide (N-(5-Sulfamoyl-1,3,4-thiadizol-2-yl)-acetamide) to inhibit the growth of other coliform-like organisms which normally give positive results in tests for *E. coli*, and, in combination, about 0.05 to 0.15% cysteine and about 0.005 to 0.015 heptadecylsulfate to stimulate metabolism of *E. coli*. These are particularly important where the organism is recovered from chlorine treated effluent and the organism has been damaged and is slow to express metabolic activity.

The nutrient medium contains from about 0.05% to about 0.15% yeast extract, from about 0.15% to about 0.25% taurocholic acid, from about 0.05% to about 0.15% yeast nitrogen base, from about 0.5% to about 2.5% lactose, and from about 0.3% to about 0.75% Gelysate peptone or other suitable peptone.

A suitable substitute for yeast extract is beef extract. Suitable peptones are Gelysate Peptone from BBL and other biological peptones. Suitable visual indicators are reduced Aniline Blue and other biological pH indicators. Sodium hydroxide is used to adjust the pH of the medium to 7.4 to 7.5, preferably about 7.4.

The purpose of the yeast or beef extract is to enrich the medium in order to speed growth of *E. coli*. The essential elements of the yeast extract are water soluble vitamins.

Gelysate Peptone is a gelatine hydrolysate made by pancreatic digestion characterized by a low cysteine and tryptophane content. It is a conventional nutrient media additive and is readily available commercially. Other like materials are Trypticase, Phytone and Polypeptone.

The purpose of the taurocholic acid is to aid in retarding growth of gram positive organisms. Other suitable surfactants can be used for this purpose. Additional surfactants which may be added to inhibit growth of gram positive bacteria include deoxycholic acid (0.1 – 0.9%); cholic acid (0.1 – 1.0%); taurodeoxycholic acid (0.5 – 0.25%); lithocholic acid (0.005 – 0.045%); taurocholic acid (0.1 – 0.3%); Brilliant Green (0.001 – 0.008%); crystal violet (0.0001 – 0.0005%); heptadecylsulfate (0.005 – 0.1%); and Bile Salts (0.08 – 0.5%).

The purpose of the yeast nitrogen base is to provide additional vitamins and a source of trace mineral elements.

The purpose of the lactose is to provide a source of carbon and energy for growth. Lactose is important in the medium as it is fermented by *E. coli* which produces acid that is measured by the pH indicator to indicate the presence of *E. coli* metabolism.

The purpose of the heptadecylsulfate is to act with cysteine to enhance *E. coli* activity. Those are particularly important when the specimen is from sewage water which has been treated with chlorine to damage the *E. coli* organism. Such damaged organisms are slow to metabolize in the medium and require extra nutrients.

The purpose of the peptone is to provide a nitrogen source for complete metabolic activity of *E. coli*.

The nutrient medium should also contain reducing agents. Suitable reducing agents are reduced cysteine and thioglycollate. The purpose of the reducing agent is to enhance *E. coli* metabolic activity particularly when dealing with damaged organisms.

The essence of this invention lies in the combined action of the two chemical inhibitors, p-coumaric acid and acetazolamide. These inhibitors act synergistically to inhibit the growth of organisms other than *E. coli*. Cysteine and heptadecylsulfate are used to enhance *E. coli* metabolism.

Growth of species of Klebsiella, Enterobacter, Aeromonas, and coliforms and coliform-like organisms which result in high yields of positives by conventional detection methods is inhibited by these chemical inhibitors in the process described below.

The concentration of p-coumaric acid can be from about 0.03% to about 0.08% and it is most effective at 0.05%. If the concentration is too low, a higher yield of unwanted false positives occurs. If the concentration is too high, a lower yield of positives occurs. This concentration is effective at the high (44.5° C) temperatures used.

Acetazolamide can be used in concentrations from about 0.05% to about 0.20%, but is most effective at a concentration of 0.10%. Varying the acetazolamide concentration has essentially the same effect as varying the p-coumaric acid concentration.

These two chemicals must be present in the broth and must be within the concentration specified at the high temperature used. The concentrations may be increased if lower broth temperatures are used. In chlorinated water samples, cysteine and a surfactant, such as heptadecylsulfate, must be provided to enhance the activity of *E. coli*.

OPERATION

The medium is made double strength or other high concentration as dictated by laboratory protocol. For example, twice the normal amount of ingredients per unit volume are put into solution, so that subsequent dilution by an equal volume of sample will result in the proper singlestrength concentration. Similarly three times the normal amount may be dissolved, per unit volume and then 2 ml of sample per each ml of concentrated broth would be used. The medium is dispensed in a conventional test tube or container. It is then inoculated with an appropriate amount of water sample so that the final ingredient concentration will be that specified in Example I.

The inoculated medium is incubated in the test tube or other containers at 35° C for 6 hours. The temperature may be 35° to 38° C and the time may be from 4 to 6 hours. The containers of incubated medium are then incubated at 44.5° C for an additional 10–12 hours. The temperature can be 44°–46° C and the time can be 10–12 hours. At the end of the total 18–20 hour maximum incubation period, the tubes or containers are examined for growth and production of blue color.

It is necessary that pre-incubation be performed for 4 to 6 hours at 35° C. Failure to employ this preincubation period will result in lower yields of positives. This fact is especially significant where chlorination of the water may have occurred immediately prior to sampling.

If enumeration of *E. coli* present in the sample is desired, a set of tubes may be inoculated in most probable number (MPN) fashion as described in *Standard Methods for the Examination of Water and Waste Water*, Edition 13, and the number of organisms determined by statistical evaluations. The process would be performed using this described broth instead of the recommended broth, using no Durham tubes to detect gas, and test results would be read after 16–20 hr. incubation. The mechanics of the MPN test would remain as described in *Standard Methods*.

EXAMPLE I

*E. coli* detection broth is prepared by thoroughly mixing the following components as described. This example describes preparation of 200 ml of 2X broth:

Combine 8 g lactose, 2 g Gelysate Peptone, 0.4 g yeast extract, 0.4 g yeast nitrogen base, 0.8 g taurocholic acid, 0.4 g cysteine, and 4 ml of 1% heptadecylsulfate solution in 150 ml of distilled water. To 75 ml of this solution add 0.4 g acetazolamide, 0.2 g para-coumaric acid, and 0.9 ml 10N sodium hydroxide. Stir to dissolve completely. Add back to remaining broth and adjust pH to 7.15 – 7.25. Add 8 ml decolorized Aniline Blue. pH to 7.4 q.s. to 200 ml with distilled water. Filter sterilize. When diluted with sample for use to detect *E. coli*, the final 1X concentration will be as follows:

| | |
|---|---|
| Para-coumaric acid | 0.05% |
| Acetazolamide | 0.10% |
| Yeast extract | 0.10% |
| Yeast nitrogen base | 0.10% |
| Taurocholic acid | 0.20% |
| Cysteine | 0.10% |
| Heptadecylsulfate | 0.01% |
| Lactose | 2.00% |
| Gelysate peptone | 0.50% |
| Decolorized aniline blue | 0.02% |
| Water | to 100.00% |

The reduced aniline blue indicator is made by the process described in Aldridge and Meyer application for U.S. Patent entitled SENSITIVE PH INDICATOR filed on even date herewith.

What is claimed is:

1. A composition for selectively identifying *E. coli* comprising:
   a. a source of nutrients,
   b. an indicator to visually show the acid produced by metabolic activity of *E. coli* organism,
   c. an inhibitor to inhibit the growth of other coliform-like organisms which normally give positive results in tests for *E. coli*, said inhibitor being a combination of acetazolamide and para-coumaric acid, and
   d. an enhancer to stimulate activity of *E. coli* organism.

2. The composition of claim 1 wherein the inhibitor is a combination of 0.10 to 0.30% acetazolamide and 0.01 to 0.15% para-coumaric acid.

3. The composition of claim 1 wherein the indicator is reduced aniline blue.

4. A composition for selectively identifying *E. coli* comprising:

a. from about 0.03% to about 0.08% para-coumaric acid,
b. from about 0.05% to about 0.20% acetazolamide,
c. from about 0.05% to about 0.15% yeast extract,
d. from about 0.05% to about 0.15% cysteine,
e. from about 0.15% to about 0.25% taurocholic acid,
f. from about 0.05% to about 0.15% yeast nitrogen base,
g. from about 0.5% to about 2.5% lactose,
h. from about 0.005% to about 0.015% heptadecylsulfate,
i. from about 0.3 to about 0.75% peptone,
j. from about 0.005% to about .025% reduced aniline blue,
k. and water to 100%.

5. A composition for selectively identifying *E. coli* comprising:
a. about 0.05% para-coumaric acid,
b. about 0.10% acetazolamide,
c. about 0.10% yeast extract,
d. about 0.10% cysteine,
e. about 0.20% taurocholic acid,
f. about 0.10% yeast nitrogen base,
g. about 2.0% lactose,
h. about 0.01% heptadecylsulfate,
i. about 0.5% peptone,
j. about 0.02% reduced aniline blue,
k. and water to 100%.

6. A method of selectively identifying *E. coli* organism comprising the steps of:
a. inoculating a specimen containing an unknown organism into a medium which comprises,
   a. a source of nutrients,
   b. an indicator to visually show the acid produced by metabolic activity of *E. coli* organism,
   c. an inhibitor comprised of a combination of acetazolamide and paracoumaric acid to inhibit the growth of other coliform-like organisms which normally give positive results in tests for *E. coli*, and
   d. an enhancer to stimulate activity of damaged *E. coli* organisms,
b. incubating the inoculated medium at about 35° to about 38° C for about 4 to about 6 hours,
c. further incubating the inoculated medium at about 44° to about 56° C for about 10 to about 12 hours,
d. observing the presence of *E. coli* organisms by change in the color of the medium.

7. The method of claim 6 wherein the *E. coli* is in a chlorinated water specimen.

8. A composition for selectively identifying *E. coli* comprising:
a. a source of nutrients,
b. an indicator to visually show the acid produced by metabolic activity of *E. coli* organism,
c. an inhibitor to inhibit the growth of other coliform-like organisms which normally give positive results in tests for *E. coli*, and
d. an enhancer to stimulate activity of *E. coli* organism, said enhancer being a combination of 0.05 to 0.2% cysteine and 0.005 to 0.02% heptadecylsulfate.

* * * * *